United States Patent [19]
Wortrich

[11] Patent Number: 5,163,900
[45] Date of Patent: Nov. 17, 1992

[54] DISPOSABLE CASSETTE SYSTEMS

[75] Inventor: Theodore S. Wortrich, Long Beach, Calif.

[73] Assignee: Surgin Surgical Instrumentation, Inc., Placentia, Calif.

[21] Appl. No.: 596,219

[22] Filed: Oct. 12, 1990

Related U.S. Application Data

[63] Continuation-in-part of Ser. No. 324,018, Mar. 16, 1989, Pat. No. 4,963,131.

[51] Int. Cl.$^5$ ............................................. A61M 1/00
[52] U.S. Cl. ........................................ 604/30; 604/34
[58] Field of Search .................... 604/30, 34, 35, 250

[56] References Cited

U.S. PATENT DOCUMENTS

| | | | |
|---|---|---|---|
| 4,713,051 | 12/1987 | Steppe et al. | 604/34 |
| 4,798,580 | 1/1989 | DeMeo et al. | 604/34 |
| 4,963,131 | 10/1980 | Wortrich | 604/34 |
| 5,106,366 | 4/1992 | Steppe et al. | 604/34 |

Primary Examiner—Paul J. Hirsch
Attorney, Agent, or Firm—Merchant, Gould, Smith, Edell, Welter & Schmidt

[57] ABSTRACT

A system for controlling the irrigation and aspiration functions in flow lines cooperative with a surgical control console employs a reusable receiver within which a disposable cassette is insertable. The cassette includes lines which must be sterile for each user, but cooperates with elements in the receiver to which it is detachably engaged. Slider bars within the receiver are arranged to transmit clamping forces against interior flexible lines such that shortened and simplified flow paths are used.

19 Claims, 6 Drawing Sheets

DISPOSABLE CASSETTE SYSTEMS

CROSS-REFERENCE TO RELATED APPLICATION

This application is a continuation-in-part of U.S. patent application Ser. No. 07/324,018, filed Mar. 16, 1989, now U.S. Pat. No. 4,963,131 entitled DISPOSABLE CASSETTE FOR OPHTHALMIC SURGERY APPLICATIONS, and assigned to the assignee of the present invention.

BACKGROUND OF THE INVENTION

Disposable cassette systems are widely used, particularly in medical applications involving the handling of fluids that interact with biological systems. Examples are to be found in U.S. Pat. Nos. 4,493,695, 4,627,833, and 4,713,051.

Where blood is the fluid being transferred, the dangers of contamination are high, and consequently it is generally preferred to utilize disposable tubing and fluid transfer systems rather than attempt to sterilize part or all of the fluid handling system for each use. Incorporation of the essential elements in a relatively low cost cassette minimizes removal and handling time and the dangers of an incorrect setup. The same is true in fluid interchange systems used for ophthalmic surgical applications, such as irrigation and aspiration systems of the type sold by Site, a Johnson & Johnson subsidiary, under their Model No. TXR, and by CooperVision, now Alcon, under the Model 10,000. The Model 10,000 is essentially described in U.S. Pat. No. 1,713,051 to Steppe, et al. and represents a cassette adaptation of an earlier Model 8000 that employed loose tubing sets with peristaltic pumps and passed waste matter to a plastic bag. The Site cassette, as evidenced by U.S. Pat. No. 4,627,833 to Cook, disposes irrigation and aspiration lines in a rectangular package having an attached rigid collection vessel. Within the cassette body, there are complex flexible tubing paths. In both systems internal flexible lines are juxtaposed so that clamp actuators in the console may pinch exposed lines against internal surfaces to stop flow, after the cassette is inserted. In operation of both systems, sterile irrigation fluid from a source is fed by gravity to the operative site, and aspirated therefrom back to a collection unit.

In the Site device, the aspiration line is coupled to a reciprocating diaphragm pump, whereas in the CooperVision system, the coupling is to a peristaltic pump. The Coopervision cassette is configured in a conventional fashion to have a semicircular boss against which the rollers of the peristaltic pump may press the irrigation line so as to establish the needed transfer force on the irrigation fluid. The Site unit couples the aspiration line into a rigid container attached directly to the cassette, within which a lowered pressure is created by a suction line from the pump.

In parent application, U.S. patent Ser. No. 07/324,018, now U.S. Pat. No. 4,963,131 to the instant application, it is shown that the use of internal sliders within a cassette body to transfer force from an external clamp actuator internally into a selected location or locations within the cassette has a number of particular advantages. By confining the area of repeated flexure of the transfer lines to well within the body of the cassette, the danger of contamination of sterile flows upon the occurrence of cracks or pinholes in the line due to repeated flexure is greatly minimized. Also, the line geometries within the cassette are straightened, shortened and simplified by virtue of the degrees of design freedom that are available. Thus a number of operative and mechanical advantages are obtained at no substantial increase in cost.

The cost of disposable cassettes is, however, an item of constant concern as health care expenses continue to mount. A dramatic decrease in the cost of disposable units, without sacrifice of sterility or operative advantages is greatly to be desired.

SUMMARY OF THE INVENTION

Substantial advantages are achieved in accordance with the invention by apparatus and methods which use separate, interacting cooperative units and segregate the supply or irrigation function from the aspiration, pumping and control functions. A receiver structure is inserted in the cassette receiving surface or receptacle of the system and includes means to provide a reusable flow path for the handling of aspiration fluid. Such means comprise interior and exterior fittings for coupling lines between the operative site and a collection receptacle. However the geometry is arranged such that an open sided interior volume is defined in the receiver. A smaller second disposable unit conforms to and engages within the interior volume in the receiver structure. The disposable unit includes fittings for lines connecting a sterile fluid source to the operative site. The combination of receiver and cassette includes those fittings and internal tubing needed for connection of the aspiration lines to a vent or other form of vacuum control on the system console. Internal sliders in the receiver act upon lines in the receiver and cassette disposed to simplify and shorten the internal tubing geometry and provide contamination safeguards. Thus a reusable conduit system is provided that connects the aspiration flow path from the handpiece to the waste collection unit, while sterile fluid pathways are incorporated in a smaller disposable cassette. The net monetary result is that the usage cost can be distributed over a number of procedures so that the average cost is reduced by a substantial factor.

In a more particular example of the invention, a receiver unit having a semicircular boss for engagement against a peristaltic pump includes an interior aspiration line fitting, a flexible aspiration line traversing the face of the semicircular boss, and an outlet aspiration fitting, together with exterior guides for fitting within the cassette opening in the system console. The receiver also includes a pair of sliders, an interior side guide structure about an open-ended receptacle portion, and a vacuum control line coupling section. The two sliders, interior aspiration line fitting, and an interior vent line fitting are presented by the receptacle portion along an interface region. A smaller disposable plastic cassette is insertable into the receiver structure, and includes, at its forward edge engaging the interface region, an aspiration line connector mateable into the interior aspiration line fitting in the receiver, and a vacuum control line connector mateable into the vacuum control coupling. Internal recessed aspiration and irrigation line sections are disposed between the ends of the sliders and interior backup surfaces when the cassette is inserted. External fittings are provided for aspiration line input from the operative site, sterile fluid input from a source and sterile fluid output to the operative site. With this arrangement all the needed internal functions and connections are provided but the segregation of parts within separate units enables the sterile pathways to be assured with substantially reduced cost.

In another specific example in accordance with the invention, the receiver is shaped to be received by the cassette engagement surface of a console that includes a diaphragm type pump. The receiver has forward extending vacuum and vent line fittings for coupling to the pump and the vent port respectively when inserted. The receiver also includes a pair of sliders, one of which is engageable at its interior end against an aspiration line section traversing an adjacent backup surface. The receiver in this instance includes a small interior volume, open ended at the outer end, in which a small rectangular cassette having only an interior irrigation line traversing a backup surface is contained. Input and output fittings for lines to a sterile source and the operative site respectively extend from the outward face of the inserted cassette.

The aspiration line from the handpiece extends to the anterior surface of the receiver, where internal connections are made to the pump fitting and to a flow line to a detached waste canister. The line to the spaced apart waste canister is a direct connection via the receiver to the suction line, while a return line from the canister passes across a backup surface engageable by a clamp, and also is in communication with the pressure sensing line on the console. Thus normal aspiration flows pass into the canister under the suction created, but when the suction is at an undesirable level the system can operate the clams to terminate aspiration. Sterile flows are segregated from non-sterile flows and net costs are substantially reduced, as in the prior case.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
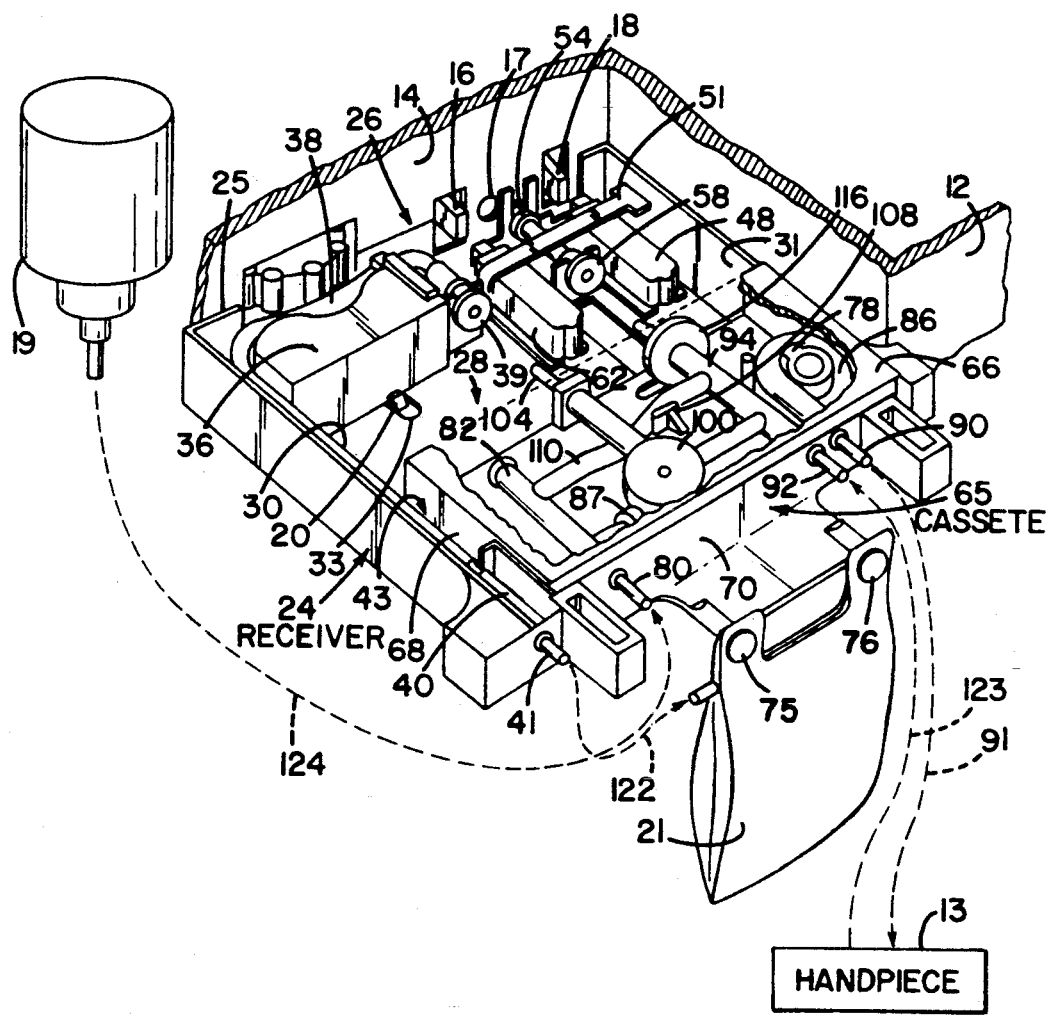
FIG. 1 is a perspective view, partially broken away, of one example of a receiver and cassette system in accordance with the invention for use in ophthalmic applications.

A modular tubing and interconnect system 10 in accordance with the invention is shown as adapted for use with the console 12 of a widely used commercial type of irrigation/aspiration system for ophthalmic surgery, specifically the CooperVision (now Alcon) Model 10,000. Only certain functions of this console 12 that are relevant to the pathway and control of flow of fluids via a handpiece 13 are shown, and these only in generalized form. The console 12 includes a cassette receptacle 14 of generally rectangular form, having a front opening leading to an inner edge along which are disposed a number of operative elements. These comprise a peristaltic roller pump 15, a shunt line actuator 16, a vacuum control system (VCS) line 17 and an irrigation line actuator 18. Although other orientations may be used, the receptacle 14 in practice has a principal length in the horizontal direction. The horizontal direction, as well as the anterior (front face) and posterior (internal face) regions of the receptacle 14 may be referred to for convenience, it being understood that this is by way of example only and that other orientations are feasible. The VCS line 17 feeds to a pressure sensor system which is used to control pump rate.

Assuming this orientation, the peristaltic roller pump 15 rotates about a vertical axis, and its periphery describes an arc that protrudes through the posterior edge of the receptacle 14, to provide the characteristic roller pumping action on a adjacent flexible line, as described hereafter. A shunt line actuator 16 and an irrigation line actuator 18 comprise bar elements moving in the posterior-anterior direction when actuated, to close off flexible lines disposed in their path, or in the path of slider mechanisms as disclosed in applicant's previously filed application, U.S. patent Ser. No. 324,018 now U.S. Pat. No. 4,963,131. The surgeon also has a foot control (not shown) by which he can stop the pump or reduce the vacuum. These relationships are all established within the commercial version of the system, and reference can be made to the published materials pertaining to the system Model 10,000 if further discussion is needed. In general terms, however, flow under gravity of sterile irrigation fluid from a bottle 19 passes through a flexible line which can be closed by the irrigation line actuator 18 before it passes to the handpiece 13. Fluid, tissue and debris from the surgical site are extracted from the operative site via the handpiece 13 because of the differential pressure (suction) created by the peristaltic roller pump 15 as it acts on the adjacent flexible line. The pump 15 passes the withdrawn aspiration fluid outward from the cassette to a waste container 21. The VCS line 17 feeds to a sensor which is used to vary pump speed to modulate the amount of suction, as controlled by the surgeon or other operating staff. In this system a flexible shunt line between the irrigation and aspiration flow is, as described below in greater detail, normally closed off by the shunt line actuator 16. It may be opened however to permit backflow of irrigation fluid in the handpiece 13 so as to clean out adhering debris and provide instant vacuum relief.

The receptacle 14 also includes engagement latches 20, for releasably receiving and retaining an enclosed cassette at the underside thereof.

In accordance with the present invention, two separate units having separate functions and durations of use are engaged within the receptacle 14 in partially nesting relation. A reusable receiver 24, which is generally rectangular in plan view (FIG. 2) fits within the receptacle 14. The receiver 24 has a leading or inserted edge 25 that penetrates into the posterior portion of the receptacle 14 so as to place various elements in individual operative relationship to the roller pump 15, actuators 16 and 18 and VCS line 17. The receiver 24 thus may be said to have, when inserted, a leading edge interconnect portion 26 and an interior cassette receiver volume 28. The cassette receiver volume 28 is of generally rectangular form and configured to accept, guide and retain a disposable cassette in position. A small upstanding ledge 29 along the anterior lower edge permits a cassette to be held releasably when inserted. Side rails 30, 31 provide guidance for the cassette, and latch openings 33 in the bottom engage to the latches 20 in the receptacle 14 for releasable detention when the receiver 24 is fully inserted.

The interconnect portion 26 of the receiver 24 includes a semicircular backup member 36 opposite the roller pump 15 at the inserted edge. An aspiration line 38, comprising a flexible tubing, extends longitudinally along the backup member 36, from a female aspiration fitting 39 at the anterior side of the interconnect portion 26. From the backup member 36 the aspiration line 38 extends along one edge of the receiver 24 to an anterior (on the receiver) output fitting 40, to which is coupled an aspiration output port 41. Between the backup member 36 and the output fitting 40 the aspiration line 38 passes within a channel 43 extending between the side rail 30 and the edge of the receiver 24.

The inserted edge of the receiver 24 also includes a first recess 46, in the bottom surface, leading to a guide slot 47 in which a first or irrigation slider 48 is located so as to be slidable in the posterior-anterior direction. The first slider 48 includes a posterior end surface 49 for engagement by the actuator 18, and a terminal anterior ridge 50 for clamping an associated length of flexible tubing. A transverse retainer strap 51 holds the slider 48 in position. The interconnect portion 26 of the receiver 24 further includes a VCS grommet 54, adjacent the first slider 48, comprising an integral female fitting 57 facing the pressure control line 17, an extension tubing lying in the anterior direction from the fitting 57, and a second integral female fitting 58 facing in the anterior direction from the interconnect portion 26. Between the VCS grommet 54 and the aspiration female fitting 39 a second recess 60 is provided in the lower wall at the inserted end of the receiver 24. The second recess 60 leads to a second guide slot 61 in which a second or shunt slider 62 is movable. The second slider 62 also includes an end surface 63 for engagement by the shunt actuator and a terminal ridge 64 for clamping an associated flexible tubing.

The receiver 24 and its component parts may be made wholly of metal, of plastic, or of different materials, inasmuch as this structure is not required to be wholly sterile. Consequently, the receiver 24 may be kept in place for multiple surgical procedures, while replacing only the disposable sterile cassettes 65.

The cassette 65 comprises a substantially rectangular cassette body 66 having flat surfaces 68 along its sides for engaging the side rails 30, 31 of the receiver 24. The low ledge 29 along the anterior lower edge of the receiver 24 holds the cassette 65 in position when inserted. The cassette body 66 is substantially open at its inserted (posterior) edge, but at its anterior edge includes a wall or bar 70 received in retainer blocks 72 at each end, within which bar 70 are secured the fittings for various tubing sections. In the intermediate region of the anterior portion of the cassette body 66, a lower horizontal extension 74 serves as a platform for a pair of posts 75, 76 to which the waste bag 21 may be detachably secured.

Internally, the substantially flat region of the cassette body 66 between the side sliders 68 and the holder bar 70 includes a first backup surface 78 aligned with the first slider 48 when the cassette body 66 is inserted in the receiver 24. The backup surface 78 comprises a circular ring, about which an irrigation line may be wrapped, as described below. The irrigation flow path extends between an irrigation input port 80 held in the bar 70 and attached to an irrigation manifold 82 that includes an irrigation line junction 84 to which an internal flexible irrigation tubing 86 is coupled. The irrigation line 86 extends to the opposite side of the cassette 65, via a one way valve 87, then passing about the circular member that includes the backup surface 78. The irrigation line 86 therefrom connects to an output fitting 88 that is retained in the holder bar 70 and is coupled to an output port 90.

The aspiration line 91 from the handpiece 13 is attached to an aspiration input port 92 coupled to an aspiration manifold 94 having a pair of junctions. A first of these junctions 96 leads to a first interior aspiration line 97 and then to a second interior aspiration line 98 via an intervening flow dampener 100. The second aspiration line 98 is coupled to an aspiration fitting that leads to an adjacent aspiration port 104 that serves as a male member, engaging within a female member on the receiver 24. In the region between the irrigation manifold 82 and the aspiration manifold 94 is disposed a backup post 108 for a shunt line 110 that extends between a shunt line junction 111 on the irrigation manifold 82 and an opposed junction 112 on the aspiration manifold 94.

The aspiration manifold 94 also is coupled at its posterior end to a hydrophobic filter 116 that leads to a male vacuum control port 118 for insertion into the anterior fitting 58 in the receiver 24. In this example the hydrophobic filter 116 is of circular outline and a slot opening 120 is provided in the wall of the cassette body 66 to permit a commercial rather than a specially modified shape of hydrophobic filter to be used.

Figure 2:
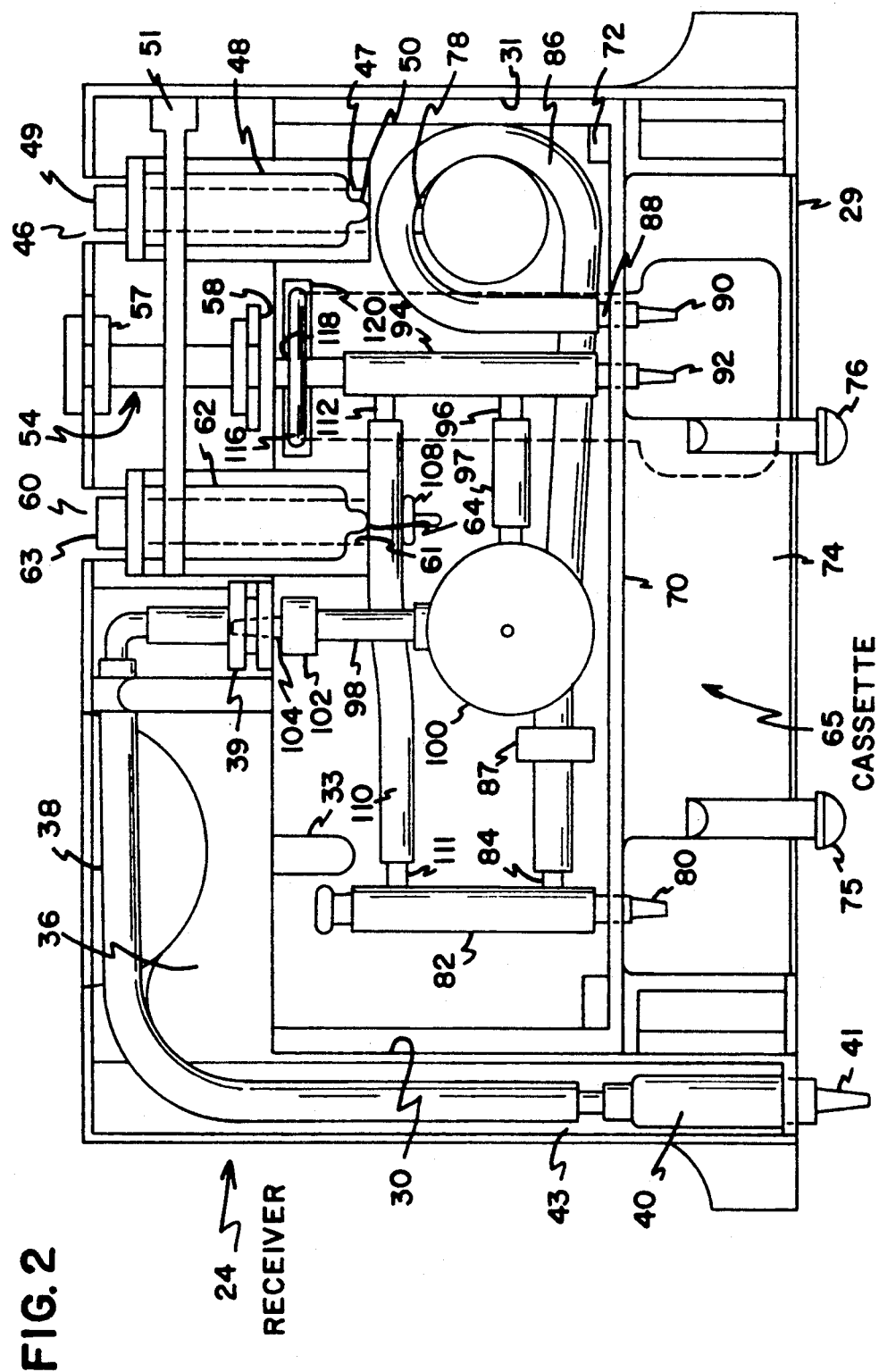
FIG. 2 is a perspective plan view of the receiver and cassette units in the arrangement of FIG. 1, with the top cover removed.
Figure 3:
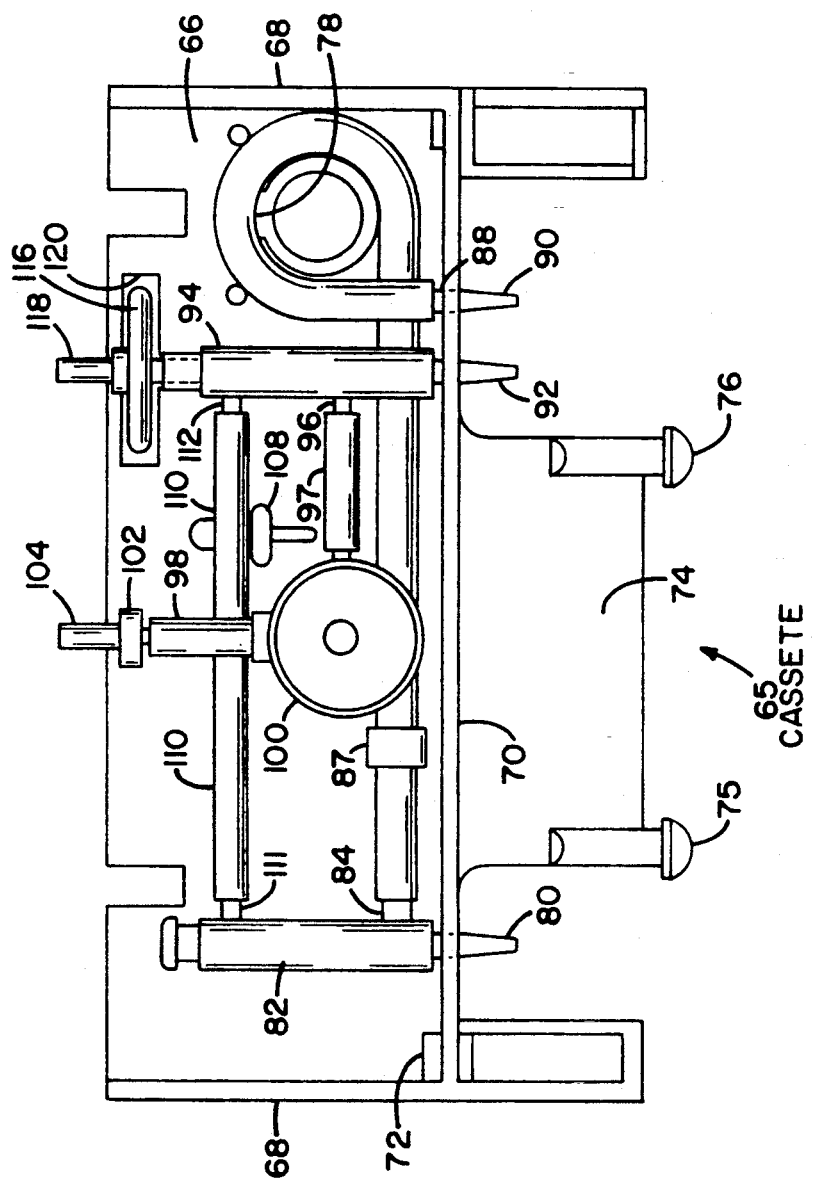
FIG. 3 is a plan view, as seen without a top cover, of the disposable cassette to seat within the receiver unit of FIG. 1 and 2.

The tubing interconnect system of FIGS. 1-3 is depicted as used with the CooperVision Model 10,000 because of the number of control functions that are included in that system. These include the peristaltic pump, shunt control, vacuum control system, and irrigation flow control that make available to the surgeon particular operating modes through use of the handpiece 13 and a foot control. In operating the system, the receiver 24 containing the aspiration tubing 38 spanning the semicircular backup member 36 is first inserted into the receptacle 14 in the console 12. The receiver 24 is guided directly into position by the side rails 30, 31, until the openings 33 in the bottom of the receiver 24 engage the latches 20 in the console 12. With the receiver 24 engaged in position, the end surface 49 of the first slider 48 directly opposes the irrigation line actuator, the VCS grommet 54 mates with the VCS line 17 in the console, and the second slider 62 is engaged by the shunt line actuator 16 at its end surface 63. Concurrently, the peristaltic pump 25 engages the aspiration tubing 38 against the backup surface 36, enabling pumping when the pump 15 is rotated. A waste line 122 is coupled to the output port 41 and feeds into a waste collection bag 21 when it is attached. The handpiece 13 is connected by an irrigation feed line 123 for sterile solution and the aspiration return line 91. The mechanism thus far described therefore reconfigures the system console 12, and forms a modified operating system. The anterior surface of the interconnect portion 26 of the receiver 24 presents exposed operative parts above the cassette receiver portion 28 that are, in sequence, the terminal ridge 50 on the first slider 48, the female fitting 58 on the VCS connection, the terminal ridge 64 on the second slider 62, and the female aspiration fitting 39 coupled to the aspiration tubing 38. These members are all adapted to engage or receive portions of the disposable cassette 65.

When the body 66 of the cassette 65 is inserted in the cassette receiver portion 28 its forward or leading edge defines a posterior surface that engages the anterior surface of the interconnect portion 26. In this position, the protruding first and second sliders 48, 62 respectively are positioned to press the irrigation tubing 86 against the first backup surface 78, and the shunt line 110 against the backup post 108. The male fitting comprising the vacuum control port 118 engages in the female fitting 58 that is part of the VCS grommet 54. Concurrently the aspiration port 104 at the posterior end of the cassette 65 engages in the female aspiration fitting 39 of the receiver 24. These couplings complete the communication pathway between the aspiration manifold 94 and the aspiration line 38 leading to the output port 41 that passes matter to the waste bag 21 via the line 122.

Consequently, the system is reconfigured, with a portion of the reusable pathways being disposed in the receiver system, and all of the sterile pathways being disposed in the disposable cassette 65. The waste bag 21 is suspended from the posts 75, 76 and a feed line 124 from the sterile external source 19 is coupled to the irrigation input port 80. The external line 91 is coupled from the irrigation output port 90 to the handpiece 13 and an aspiration line 123 is coupled to the aspiration input port 92 from the handpiece 13 to complete the external connections.

In the most often used mode of operation, the shunt line 110 is held closed against the backup post 108 by the second slider 62. The first slider 48 is not actuated, leaving the flexible tubing line 86 open. Thus irrigation fluid flows from the sterile source 19 through the irrigation manifold 82, the irrigation line 86 and the irrigation output port 90 to the handpiece 13. The pump 15 rotates to aspirate tissue and fluid from the handpiece 13 back to the aspiration input port 92 through the manifold 94. The aspirated matter flows via the junction 96 through the interior aspiration lines 97, 98, and the flow dampener 100 therebetween, out through the aspiration line 38 and the receiver 24 to the aspiration output port 41 and then to the waste bag 21. During this mode of operation, the VCS fitting 17 on the console 12 provides a pressure reading to the system. If the pressure is too high the roller pump 15 is slowed down or stopped.

The surgeon also has the foot control to govern flow rates. This is a conventional mode of usage of the system during an operative procedure as the surgeon manipulates the handpiece 13 and the foot control. During this mode the second slider 62 clamps the shunt line 110 against the backup surface 108.

When the back flush mode of operation is to be used, the controls are operated and the first slider 48 is engaged to clamp the irrigation tubing 86, stopping direct irrigation fluid flow via the principal path of the handpiece. At the same time, the second slider 62 is released from the shunt line 110, opening the shunt line and providing flow through the irrigation manifold 82, the shunt line 110 and the aspiration manifold 94 back down to the handpiece 13. This momentary flow is sufficient to dislodge any matter that may have accumulated in the orifices in the handpiece. All of this flow is contained within the disposable cassette 65.

When an operative procedure is completed, the disposable cassette body 66 and associated tubing including the bacterial filter 116 are removed, and another disposable cassette body 66 with sterile tubing is placed in position. It is to be noted that the sliders 48, 62 can be used repeatedly and that since they are only in contact with a sterile cassette in its interior, there is virtually no danger of contamination even if a line should develop pinholes under repeated flexure. The VCS grommet system is not required to be sterile because of the barrier provided by the bacterial filter 116 that is replaced with every new cassette. The aspiration fitting 39, the aspiration line 38 and the receiver 24 can be sterilized periodically and reused. For example, sterilization every day before commencing procedures would be a conservative approach but would result in very significant savings. Because the tubing sections used in the back flushing make are all in the disposable and because the clamps hold lines closed when power is off, the chances of contamination are minimized.

The lengths of tubing utilized within the disposable cassette are short and follow substantially direct paths. Thus, the arrangement provided is compact and inexpensive and repeated use of the receiver enables significant cost reductions to be realized.

A different example of a system in accordance with the invention comprises the structure of FIGS. 4 to 7, intended for use with a unit of the "TXR System" type sold by Site Microsurgical Systems, as generally exemplified by U.S. Pat. No. 4,627,833 to Cook. That patent, it should be noted, does not correspond to the present Site unit commercially available, in its internal configuration. In the Site irrigation and aspiration unit 125 seen only on FIG. 4, a pair of occluder bars 126, 127 are positioned spaced apart at a lower level, and suction and vent ports 128, 129 are positioned at a higher level. The Site cassette which is inserted against this portion of the console includes openings spaced to face the occluder bars, at their lower level, and ports to mate with the vent 129 and suction 128 ports extending from the upper level openings in the console face. The Site cassette comprises a substantially rectangular upper body and a rigid cylindrically shaped collection vessel which is below it and threaded into the upper body. When this type of cassette is placed in position, one suction (aspiration) and two "infusion" (irrigation) ports extend outwardly from the front face to enable flexible lines to be coupled to the handpiece and to a supply bottle. The cassette is designed so that two internal passageways between the upper portion of the cassette and the collection vessel attached to the underside. The collection vessel must be rigid and sealed, because the suction drawn by the system pump at the console is communicated via one line through an interior port into the collection vessel, and then via another line and interior port to the handpiece. The venting control couples into this flow path so as to modulate the level of suction.

In contrast to the Site device, the present construction utilizes a separate receiver, an insertable disposable cassette, and also a separate and spaced apart collection vessel. The collection vessel is not directly coupled to the cassette but is attached at a different region on the housing, where it is conveniently separately replaceable as desired.

Figure 4:
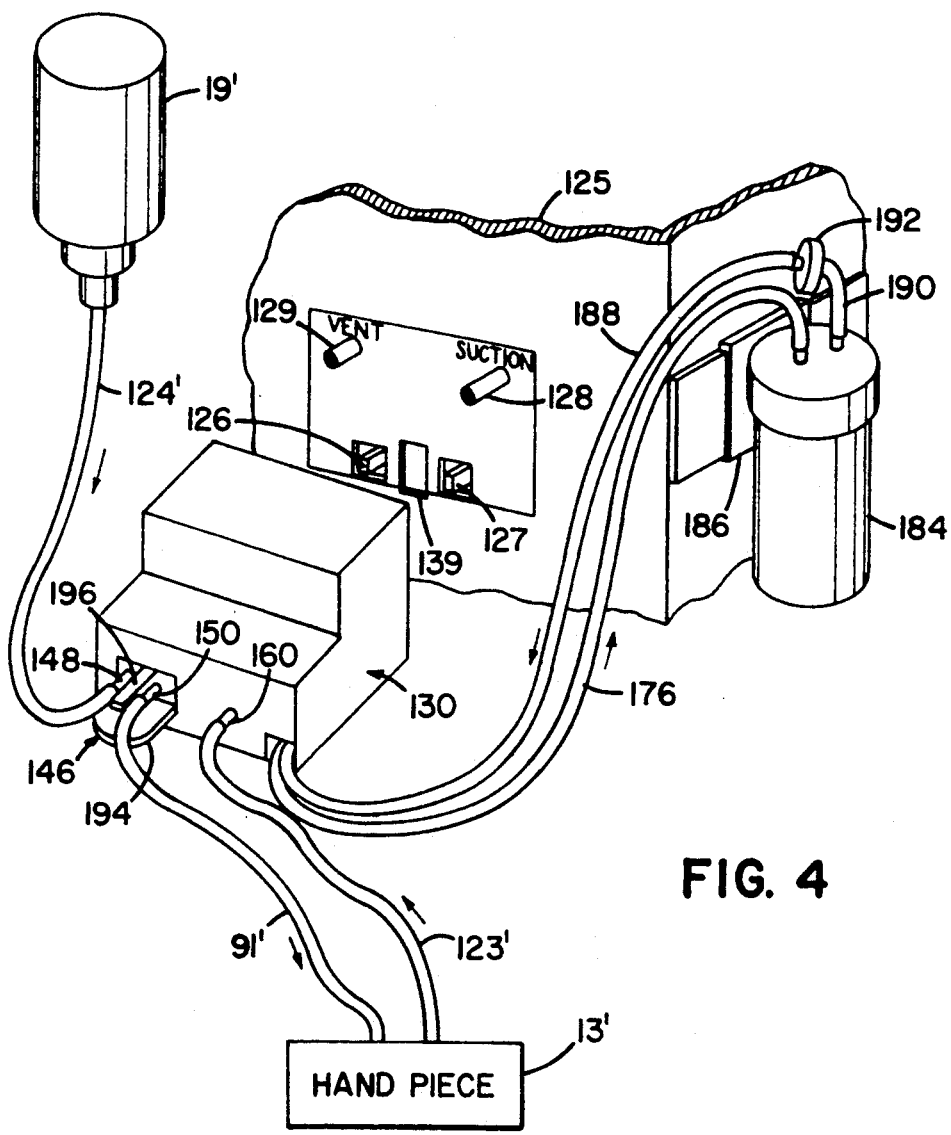
FIG. 4 is a perspective view of a different form of receiver and cassette system in accordance with the invention showing the structure adjacent a portion of a console to which it is to be attached.
Figure 5:
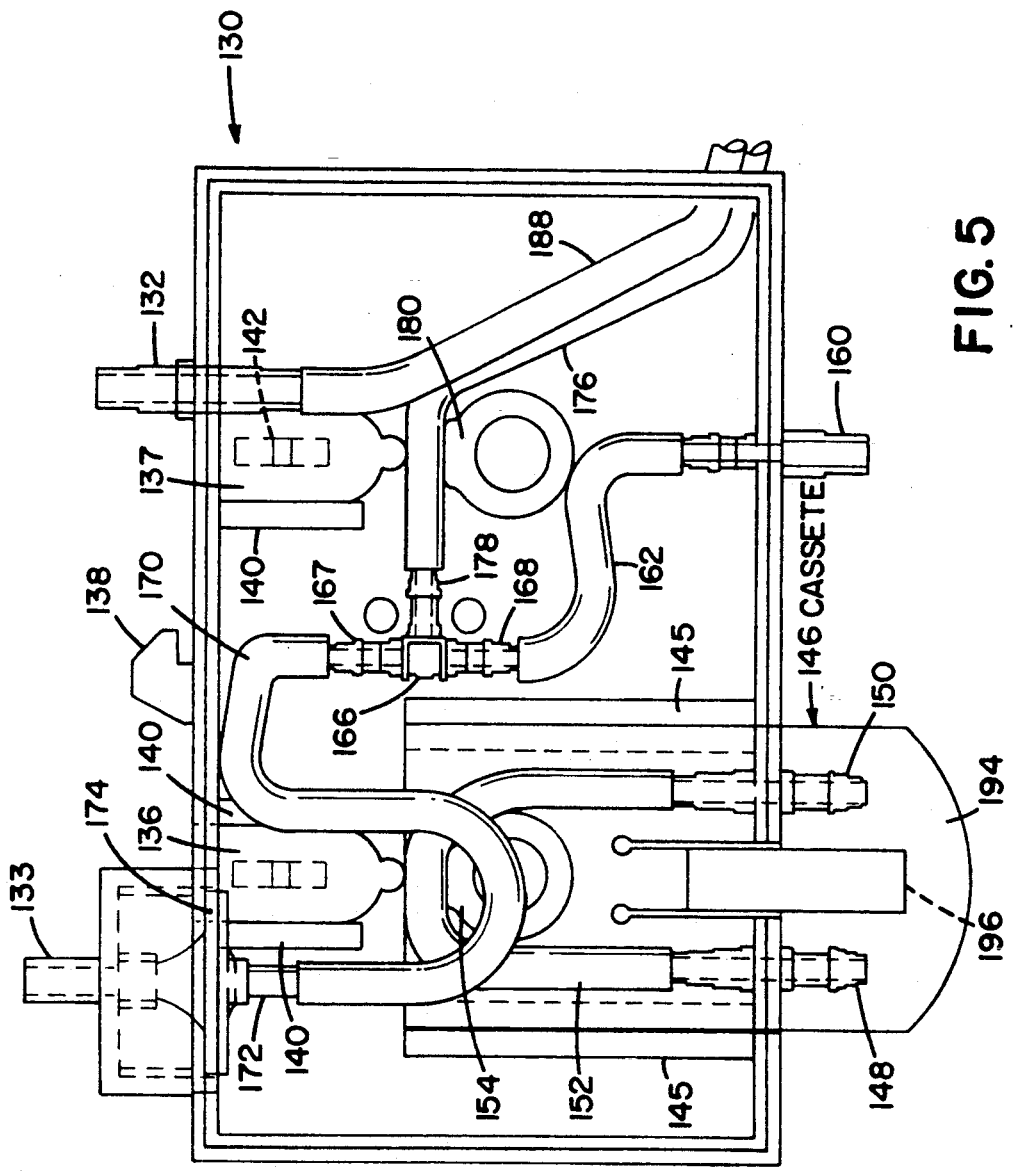
FIG. 5 is a plan view, with cover removed of the arrangement of FIG. 4, showing the disposition of the receiver and cassette when the cassette is engaged.
Figure 6:
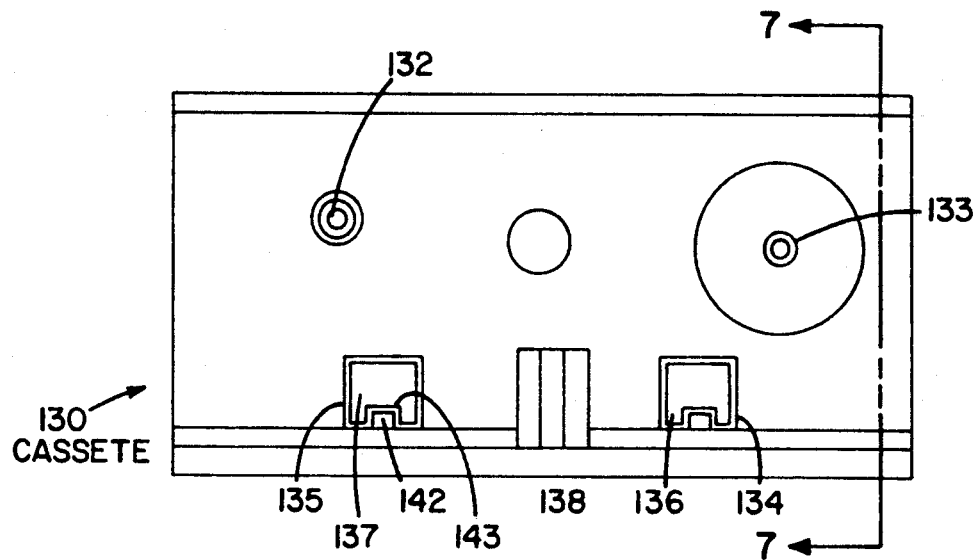
FIG. 6 is a back view, of the receiver and disposable cassette in the system of FIG. 4 and 5.
Figure 7:
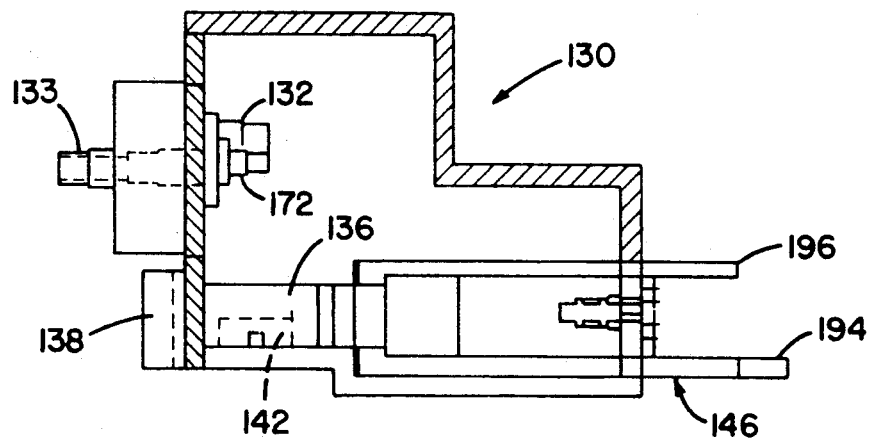
FIG. 7 is a side sectional view of the receiver and disposable cassette of FIGS. 4 to 6 without the tubing included.

Referring now to FIGS. 4 to 7, the receiver 130 is shaped as a generally rectangular frame having an insertable posterior side engageable against the receiving surface on the wall of the console 125. The posterior side includes a male vacuum port 132 and a male vent port 133 in spaced apart relation at an intermediate level and two apertures 134, 135 at a lower level for registry with the occluder bars 126, 127 of the console 125. First and second sliders 136, 137 are seated in the receiver 130 between side walls 140 and include underside projections 142, as best seen in FIG. 6, within slots 143 in the bottom the sliders 136, 137. Thus the sliders 136, 137 can reciprocate under internal forces in the posterior-anterior direction, making contact with the associated actuator 126 or 127 through the apertures 134, 135, respectively. A latch 38 on the posterior end of the receiver 130 fits within an aperture 139 in the face of the console 125 to hold the receiver 130 in position in a releasable manner.

The interior of the receiver 130 body includes an opening 140 at the anterior side bounded by side rails 145, for guiding a small disposable cassette 146 into position in the interior volume between the rails 142, 143. The cassette 146 is of generally rectangular form and includes a pair of externally accessible ports 148, 150 for coupling of exterior lines to a source of sterile irrigation fluid and to a handpiece, as described in the prior example. An interior U-shaped flexible line 152 fitting on the posterior side of the ports 148, 150 joins the two flow paths and extends about a backup surface 154 facing the anterior end of the first slider 136. When the disposable cassette 146 is slid in between the side rails 145, the curved end of the flexible tubing line 152 adjacent the backup surface 154 is disposed opposite the facing surface of the first slider bar 136 in the receiver 130 to be clamped when the actuator bar 126 of the console 125 is energized.

The connections and elements in the receiver 130, however, are separately and substantially permanently coupled inside and outside the cassette 146, as best seen in FIGS. 4 to 6. An exterior flexible tubing line 123' from the handpiece 13 is coupled to the exterior of an aspiration fitting 160 in the anterior wall of the receiver 130. At the interior of the fitting 160, a first aspiration 162 connects the aspiration path to one side leg 167 of a T junction 166. The other side leg 168 is connected via a second aspiration line 170 to the interior fitting 172 at the vent 176 port 133, the interior and exterior fittings being coupled by a one way valve 174. A flexible waste line 176 from the base leg 178 of the base leg of the T junction 166 leads across a second backup surface 180 secured in the receiver 13 opposite the second slider 137, which is disposed opposite the second occluder bar 127 in the console 125. The waste line 176 is a long line which passes out of the receiver 130 to an exterior canister 184, mounted on an attachment 186 to the side of the console 125. Suction is established in the canister 184 by another long flexible line 188 which is coupled via a hydrophilic fitter 192 to a suction fitting 190, on the canister 184. If the filter 192 is wetted by the flow between lines 22-23 it blocks further aspiration, preventing waste from flowing into the console 125. The disposable cassette 146 has a protruding portion, with an underlying base 194 and a small parallel spring loaded upper handle 196. The handle 196 can be thumb depressed to release the cassette 146 when it is to be withdrawn.

This system provides a great deal of versatility and flexibility in operation, even though satisfying the requirements of the system. By separating the collection canister 184 from the cassette 125, a remote container of virtually any size can be used, and it can be interchanged during operation if filled or if any other problem arises. All the lines subject to contaminated fluid, including the line 123 from the handpiece 13, the suction fittings, and the lines 176 and 188 between the console 125 and the canister 184, and the lines leading to the vent 129 can be reused. Instead, only the very small and inexpensive disposable cassette 146 need be changed for each separate user. Consequently, the concept of reconfiguration of the machine by the use of an internal receiver, and insertion of a disposable lower cost cassette within the receiver, is valid for this and other different configurations.

While a number of forms and modifications have been described, the invention is not limited thereto but encompasses all variants and examples within the scope of the appended claims.

I claim:

1. A system for use in the cassette receiving surface of a console having flow control mechanisms for controlling the flow of sterile fluid to an operative site from a source, and the flow of non-sterile fluid from the operative site to a waste collection means, comprising:
 a receiver configured to seat against the surface and including means defining an interior volume open to the side opposite the console, the receiver including means responsive to the flow control mechanism of the console, and at least one externally accessible means for coupling non-sterile fluid to the waste collection means, and
 a disposable cassette configured to mate within the interior volume in the receiver, the cassette including external fitting means for coupling sterile fluid flows into and out of the cassette.

2. A system as set forth in claim 1 above, wherein the system includes fluid pumping means and clamping means, and receiver includes reciprocable means responsive to the flow for blocking fluid flow in response to system actuation of the flow control mechanism, and means for drawing fluid from the operative site in response to the flow control mechanism.

3. A system as set forth in claim 2 above, wherein the disposable cassette includes at least one backup surface means disposed opposite the reciprocable means and flexible tubing for sterile fluid interposed between the reciprocable means and the backup means to be clamped selectively in response to operation of the flow control mechanism against the reciprocable means.

4. A system as set forth in claim 1 above, wherein the flow control system includes pumping means and the cassette includes means coupling the non-sterile flows from the operative site to the receiver and the receiver includes means responsive to the pumping means for feeding non-sterile flows to the waste collection means.

5. A system as set forth in claim 1 above, wherein the flow control system includes pumping means and the receiver includes means responsive to the pumping means for coupling non-sterile fluid from the operative site to the waste collection means, and the cassette includes means for transferring sterile fluid from the source to the operative site under control of the flow control mechanism.

6. A system for operation with a console having a receptacle for receiving a disposable surgical cassette, the receptacle including accessible pumping means for suction, a pair of accessible actuator means for clamping flexible lines and an accessible suction flow control device, comprising:
- a receiver insertable into the receptacle, the receiver including means defining an interior volume accessible to the exterior of the console when the receiver is inserted, and a pair of slider means disposed to individually engage the different actuator means, suction tubing means positioned to engage the pumping means, and suction line means positioned to engage the suction flow, control device;
- a disposable cassette insertable into the accessible interior volume, the cassette including internal tubing means, at least one backup surface positioned to be disposed adjacent one of the slider means, with a tubing section therebetween, and the cassette further including at least two fittings for tubing connections on the side exterior to the console, the internal tubing means also being coupled to the fittings.

7. A system as set forth in claim 6 above, wherein the system comprises an aspiration/irrigation system for ophthalmic applications for control of flows of sterile fluid from a source to an operating site, and of flows of non-sterile fluid from the operating site to waste collection means, and wherein the suction tubing means in the receiver is coupled to receive the non-sterile fluid, and the internal tubing means in the disposable cassette is coupled to receive the sterile fluid.

8. A mechanism for use with an ophthalmic aspiration/irrigation system having a cassette-receiving receptacle including a roller pump disposed to engage an adjacent flexible line, a control means for a vacuum control orifice and a pair of actuators, for engaging an adjacent flexible line, the combination comprising:
- a receiver insertable within the receptacle, the receiver including backup means facing the pump roller and aspiration tubing means including a length of flexible line disposed across the backup surface, and including a first, input, internal coupling at one end and a second, external coupling at the other end, the receiver including vacuum control orifice means engageable against the control means and further comprising a line extension from the orifice means, an internal fitting coupled to the line, first slider means engageable against the actuator clamp when the receiver is inserted and extending to a spaced apart region within the receiver;
- a disposable cassette mechanism having an aspiration input fitting, an irrigation input fitting and an irrigation output fitting, the cassette being insertable in the receiver, and including second backup means disposed opposite the interior end of the slider means when the cassette is inserted in the receiver, and flexible tubing means coupled between the irrigation input and irrigation output, and interposed between the interior end of the slider means and the second backup means, and interior line means intercoupling the aspiration input line to the aspiration line fitting of the holder means, said aspiration line means including a flow dampening means therein and further being coupled to the vacuum control connection.

9. The invention as set forth in claim 8 above, wherein the receiver means includes a second slider means the cassette means includes a third backup means and a shunt line coupling the irrigation input to the aspiration input, the shunt line means incorporating a flexible line interposed between the second slider means and the third backup member in the cassette means.

10. The invention as set forth in claim 9 above, wherein the cassette means incorporates an irrigation manifold coupled to the irrigation input fitting, and an aspiration manifold coupled to the aspiration input fitting, and wherein the shunt line means intercouples the irrigation manifold to the aspiration manifold.

11. The invention as set forth in claim 10 above, wherein the cassette has an anterior position thereof when inserted and includes means for suspending a waste bag therefrom at the anterior portion.

12. The invention as set forth in claim 11 above, wherein the receiver comprises a pair of side rails disposed to engage the side edges of the receptacle when the receiver is inserted, and the receiver further comprises means for engaging to the receptacle, and wherein said cassette means includes means slidably engaging the side rails of the receiver means when inserted.

13. The invention as set forth in claim 12 above, wherein the first backup means comprises a substantially semicircular boss and wherein the receiver further comprises female fittings for the aspiration line and vacuum control system extension at an interior edge facing the direction of the inserted cassette, and wherein the cassette includes, in the aspiration line, a male fitting engaging the female aspiration fitting in the holder, and wherein the aspiration line manifold means includes a hydrophobic bacteriological filter and a male fitting engaging in the female fitting of the vacuum line extension.

14. The invention as set forth in claim 13 above, wherein the system includes a pump roller, first and second clamp actuators and suction control means disposed along an interior surface in the receptacle, and wherein the receiver includes a leading edge having the first backup surface, first and second slider ends and vacuum control orifice disposed along the inserted edge thereof for engagement with the opposing elements in the receptacle when inserted, with the female connections of the aspiration line, and the vacuum control line being disposed along an interior axis, and the slider means extending from the inserted edge of the receiver into the region of the cassette for engagement against the respective flexible lines to be engaged when the clamp actuators are energized.

15. A unit, including a disposable cassette, for installation in the cassette-receiving receptacle of a surgical console which includes in the receptacle, a peristaltic pump roller for an aspiration line, a vacuum control fitting for an aspiration line, and an irrigation control clamp, comprising:
- a first assembly for insertion in the receptacle and engagement therein, the first assembly including a semicircular backing surface positioned for engagement with the pump roller, at least one slider for sterile flow control, means intercoupling the vacuum control fitting and aspiration line traversing the backing surface;
- a second disposable assembly for insertion in the first assembly and including irrigation line means engaging the slider and including input and output fittings along the exterior edge opposite the forward edge, inserted into the first assembly.

16. The method of using sterile disposable tubing sets in conjunction with a system having a receptacle for receiving disposable cassettes, the receptacle including tubing engaging pump means, a variable position occluder accessible to a vacuum control system orifice and at least one actuator for clamping a line in an inserted cassette, comprising the steps of:

inserting a cassette receiver into the receptacle for securement in the receptacle, the cassette receiver providing interconnections to the pump, the actuator and the vacuum control orifice;

inserting a disposable cassette in the holder within the receptacle, the disposable cassette interconnecting to the , pump line, the vacuum control orifice and the clamp actuator, and interconnecting inlet and outlet lines to the cassette.

17. The method as set forth in claim 16 above, wherein the receptacle includes a second clamp actuator and the receiver transfers movement from the clamp actuator to the cassette, and wherein the cassette includes interconnection lines to the second clamp actuator.

18. A system for use in the cassette-receiving receptacle of a console having a pump and flow control mechanisms for controlling the flow of sterile fluid to an operative site from a source, and the flow of non-sterile fluid from the operative site to a waste collection means comprising:

a receiver insertable in the receptacle and including first tubing means for conducting non-sterile fluid, and means for coupling the first tubing means to the console pump, the receiver including means defining an interior volume open at the side opposite the console when the receiver is inserted, and including mechanical means movable in response to the flow control mechanism adjacent the interior volume, and a disposable cassette insertable in the interior volume, the cassette including an interior backup surface opposite to the mechanical means, and second tubing means for sterile flow interposed between the mechanical means and the interior backup surface to be closed when the flow control mechanism is moved by the flow control mechanism.

19. A system as set forth in claim 18 above, further including a remotely located waste collection means, and wherein the receiver includes an aperture and the first tubing means extends from the receiver through the aperture to the waste collection means, and wherein the system console further includes vent means, and third tubing means coupling said means engaging the receiver includes means engaging the vent means, the vent means and connected to the waste collection means via the aperture.

* * * * *

UNITED STATES PATENT AND TRADEMARK OFFICE
CERTIFICATE OF CORRECTION

PATENT NO.  :  5,163,900
DATED       :  November 17, 1992
INVENTOR(S) :  Theodore S. Wortrich It is certified that error appears in the above-identified patent and that said Letters Patent is hereby corrected as shown below:

Column 3, line 31, "clams" should read --clamp--.

Column 3, line 48, "Fig." should read --Figs.--

Column 3, line 56, "Fig." should read --Figs.--

Column 8, line 20, "make are all in" should read --mode are all in--.

Column 8, line 36, "on" should read --in--.

Column 9, line 42, insert --line-- after the word "aspiration".

Column 12, line 49, delete "," after the word "in".

Column 13, line 12, delete "," after the word "the".

Column 14, line 16, insert --of the console-- after the word "mechanism".

UNITED STATES PATENT AND TRADEMARK OFFICE
CERTIFICATE OF CORRECTION

PATENT NO. : 5,163,900

DATED : November 17, 1992

INVENTOR(S) : Theodore S. Wortrich

It is certified that error appears in the above-identified patent and that said Letters Patent is hereby corrected as shown below:

Column 14, line 25, delete "and" after the word "means".

Signed and Sealed this

Seventh Day of December, 1993

*Attest:*

BRUCE LEHMAN

*Attesting Officer*     *Commissioner of Patents and Trademarks*